US006929654B2

(12) United States Patent
Teoh et al.

(10) Patent No.: US 6,929,654 B2
(45) Date of Patent: Aug. 16, 2005

(54) NON-OVERLAPPING SPHERICAL THREE-DIMENSIONAL COIL

(75) Inventors: Clifford Teoh, Los Altos, CA (US); Michael P. Wallace, Pleasanton, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/634,176

(22) Filed: Aug. 4, 2003

(65) Prior Publication Data

US 2004/0098029 A1 May 20, 2004

Related U.S. Application Data

(63) Continuation of application No. 09/691,954, filed on Oct. 18, 2000, now Pat. No. 6,635,069.

(51) Int. Cl.$^7$ ............................................. A61M 29/00
(52) U.S. Cl. ........................................................ 606/200
(58) Field of Search ................................ 606/200, 191, 606/194, 195; 623/1.1, 1.15

(56) References Cited

U.S. PATENT DOCUMENTS

| | | |
|---|---|---|
| 4,994,069 A | 2/1991 | Ritchart et al. |
| 5,234,437 A | 8/1993 | Sepetka |
| 5,250,071 A | 10/1993 | Palermo |
| 5,261,916 A | 11/1993 | Engelson |
| 5,304,195 A | 4/1994 | Twyford, Jr. et al. |
| 5,312,415 A | 5/1994 | Palermo |
| 5,334,210 A | 8/1994 | Gianturco |
| 5,350,397 A | 9/1994 | Palermo et al. |
| 5,527,338 A | 6/1996 | Purdy |
| 5,536,274 A | 7/1996 | Neuss |
| 5,624,461 A | 4/1997 | Mariant et al. |
| 5,639,277 A | 6/1997 | Mariant et al. |
| 5,645,558 A | 7/1997 | Horton |
| 5,649,949 A | 7/1997 | Wallace et al. |
| 5,690,666 A | 11/1997 | Berenstein et al. |
| 5,766,219 A | 6/1998 | Horton |
| 5,826,587 A | 10/1998 | Berenstein et al. |
| 5,957,948 A | 9/1999 | Mariant ....................... 606/191 |
| 6,033,423 A | 3/2000 | Ken et al. ................... 606/200 |
| 6,231,586 B1 | 5/2001 | Mariant ....................... 606/191 |
| 6,322,576 B1 | 11/2001 | Wallace et al. ............. 606/191 |
| 6,638,291 B1 * | 10/2003 | Ferrera et al. .............. 606/191 |

* cited by examiner

*Primary Examiner*—Tan-Uyen T. Ho
(74) *Attorney, Agent, or Firm*—Bobins & Pasternak LLP

(57) ABSTRACT

Vaso-occlusive devices with made of non-overlapping turns of a primary coil are described. Also described are methods of making and using these devices.

23 Claims, 4 Drawing Sheets

NON-OVERLAPPING SPHERICAL THREE-DIMENSIONAL COIL

CROSS-REFERENCE TO RELATED APPLICATION

This application a continuation of U.S. patent application Ser. No. 09/691,954, filed Oct. 18, 2000, now U.S. Pat. No. 6,635,069, from which application priority is claimed pursuant to 35 U.S.C. §120, and which application is incorporated herein by reference in its entirety.

FIELD OF THE INVENTION

This invention relates to the field of vaso-occlusive devices. More particularly, it relates to a three-dimensional vaso-occlusive device made up of a plurality of non-overlapping loops.

BACKGROUND

Vaso-occlusion devices are surgical implements or implants that are placed within the vasculature of the human body, typically via-a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. Other less stiff helically coiled devices have been described, as well as those involving woven braids.

For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration—which is better suited to occlude the vessel—once the device is so placed. Ritchart et al. describes a variety of shapes. The secondary shapes of the disclosed coils include "flower" shapes and double vortices. A random shape is described, as well.

Other three-dimensional vaso-occlusive devices have been described. U.S. Pat. No. 5,624,461 to Mariant describes a three-dimensional in-filling vaso-occlusive coil. U.S. Pat. No. 5,639,277 to Mariant et al. describes embolic oils having twisted helical shapes and U.S. Pat. No. 5,649,949 to Wallace et al. describes variable cross-section conical vaso-occlusive coils.

U.S. Pat. No. 5,334,210 to Gianturco, describes a vascular occlusion assembly comprising a foldable material occlusion bag and a filled member, for example, a helical coil with a J-hook on the proximal end. The bag expands to form a diamond shape structure and the filler member inside the bag is forced into a convoluted configuration as it is advanced into the cavity of the foldable bag.

Implantable devices using variously shaped coils are shown in U.S. Pat. No. 5,537,338 to Purdy. Purdy described a multi-element intravascular occlusion device in which shaped coils may be employed. U.S. Pat. No. 5,536,274 to Neuss shows a spiral implant which may assume a variety of secondary shapes. Some complex shapes can be formed by interconnecting two or more of the spiral-shaped implants.

Spherical shaped occlusive devices are described in U.S. Pat. No. 5,645,558 to Horton. Horton describes how one or more strands can be wound to form a substantially hollow spherical or ovoid shape comprising overlapping strands when deployed in a vessel. Notably, the device as deployed must assume a substantially minimal energy configuration in which the loops making up the spherical shape overlap with (n+1) circumference length at a minimum.

Vaso-occlusive coils having little or no inherent secondary shape have also been described. For instance, co-owned U.S. Pat. Nos. 5,690,666 and 5,826,587 by Berenstein et al., describes coils having little or no shape after introduction into the vascular space.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximally extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

None of these documents disclose an anatomically shaped vaso-occlusive coil where the loops making up the three-dimensional configuration are not non-overlapping.

SUMMARY OF THE INVENTION

In one aspect, the invention includes a vaso-occlusive device comprising at least one substantially linear strand of a vaso-occlusive member wound into a stable, three-dimensional relaxed configuration comprising a plurality of non-overlapping loops, wherein said relaxed configuration self-forms upon release from a restraining member. In certain embodiments, the relaxed configuration of the vaso-occlusive device fills a body cavity or, for example, approximates the shape of sphere. The vaso-occlusive devices described herein can include any number of non-overlapping loops, for example in certain embodiments the device will have between about 6 and 20 loops while in other embodiments the device will have between about 6 and 12 loops. The vaso-occlusive devices described herein can be comprised of a metal, for example, platinum, palladium, rhodium, gold, tungsten and alloys thereof. In other embodiments, the vaso-occlusive devices described herein comprise a stainless steel or super-elastic metal alloy. In still other embodiments, the vaso-occlusive member comprises nitinol.

In other embodiments, any of the devices described herein further include additional filamentary material attached to the vaso-occlusive member. In still further embodiments, the device comprises a deployment tip attached to at least one of the two ends of the vaso-occlusive member. The deployment tip can be, for example, mechanically detachable or electrolytically detachable (e.g., by the imposition of a current on the pusher).

In another aspect, the invention includes a method of occluding a body cavity comprising introducing any of the vaso-occlusive devices described herein into a body cavity (e.g., an aneurysm).

In yet another aspect, the invention includes a method of making a non-overlapping three-dimensional vaso-occlusive device described herein, the method comprising (a) winding a substantially linear strand of a vaso-occlusive member around a winding mandrel, said winding comprising a winding pattern that produces a non-overlapping three-dimensional vaso-occlusive device described herein; and (b) heating the mandrel and vaso-occlusive member to produce said vaso-occlusive device. In certain embodiments, the winding pattern approximates a Figure 8 shape or an hourglass shape. In other embodiments, the winding mandrel is a three-dimensional structure (e.g., approximate sphere, cube, cylinder, tetrahedron). Further, the mandrel may include grooves adapted to fit the substantially linear strand and/or pins on the surface thereof (e.g., a winding mandrel comprising 3 intersecting posts which form a 6 post structure and wherein each post is at approximately 90 relative to the adjacent posts). One or more pins may have the same cross-section (e.g., shape such as round or square, diameter, etc.) or, alternatively, each pin may have a different cross-section.

These and other embodiments of the subject invention will readily occur to those of skill in the art in light of the disclosure herein.

DESCRIPTION OF THE INVENTION

Figure 1:
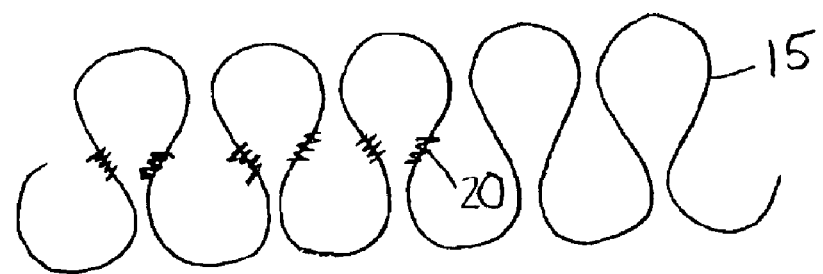
FIG. 1 depicts an exemplary Figure 8 pattern for winding a device according to the present invention. As shown, the loops making up each half of the Figure 8 are of approximately equivalent diameter.

Vaso-occlusive devices, particularly coils, are described. Upon deployment from a restraining member, the devices described herein self-form into a relaxed, three-dimensional configuration approximating an anatomically cavity. The three-dimensional configuration is made up of a plurality of loops of a first configuration. However, unlike other three-dimensional vaso-occlusive devices, the loops of the wire making up the three-dimensional configuration of the device as deployed do not overlap. Preferably, the loops do not overlap with each other or with themselves. Methods of making and using these devices also form an aspect of this invention.

Advantages of the present invention include, but are not limited to, (i) reducing or eliminating rotation upon deployment; (ii) reducing or eliminating whipping upon deployment; (iii) providing vaso-occlusive devices that readily and substantially conform to fill a target vessel in a relaxed configuration; and (iv) providing methods and materials for making these non-overlapping vaso-occlusive devices.

All publications, patents and patent applications cited herein, whether supra or infra, are hereby incorporated by reference in their entirety.

It must be noted that, as used in this specification and the appended claims, the singular forms "a", "an", and "the" include plural referents unless the content clearly dictates otherwise. Thus, for example, reference to "a coil" includes a mixture of two or more such devices and the like.

The self-forming, non-overlapping three-dimensional coil designs of the present invention are particularly useful in treating aneurysms. The non-overlapping loop design described herein provides an improvement over known devices, for example in terms of ease of deployment. Available three-dimensional coils are made up of a plurality of overlapping and intertwined loops. Upon deployment from a substantially linear configuration these devices often rotate or whip undesirably during deployment. Whipping refers to the phenomena where a device stores energy imparted by a user and then releases the energy very quickly. For example, vaso-occlusive devices are often deployed and manipulated at the target site using a guidewire controlled by the operator at a proximal location. Whipping occurs when the rotation imparted by the operator on the guidewire does not result in the same 1:1 rotation of the distal end of the device. Rather, the device stores up the rotational energy and then may suddenly release the energy and rotate suddenly in a short time. Rotation, whipping and other problems associated with available vaso-occlusive devices can impede formation of the three-dimensional relaxed configuration. In contrast, the non-overlapping configuration of the devices described minimizes rotation and whipping upon deployment and promotes formation of a three-dimensional configuration that substantially conforms to the target vessel.

Described herein are vaso-occlusive devices having a relaxed three-dimensional configuration in the approximate shape of an anatomically cavity. The three-dimensional configuration is made up of non-overlapping loops. Further, the approximately diameter of the relaxed configuration preferably conforms to the target vessel in which is deployed. As used herein, the "first configuration" or "primary configuration" refers to the structure obtained when a wire is shaped into a coil, for example, as a strand of a linear helically wound coil. The "secondary configuration" refers to the structures obtained when at least one strand of the first configuration is further shaped, for example, by winding around a mandrel. The relaxed configuration refers to the three-dimensional configuration assumed by the secondary configuration after is has been deployed from the restraining member (e.g., catheter). A device may have multiple relaxed configurations, for example depending on whether it is deployed into a body cavity, the size of the body cavity, etc. The relaxed configuration typically comprises a three-dimensional structure made up of non-overlapping loops of the first configuration. The structure may be composed of any number of non-overlapping loops. In certain embodiments, the three-dimensional configuration has between about 4 and 40 loops, more preferably between about 6 and 20 loops and even more preferably, between about 6 and 12 loops. The non-overlapping loops can form an open shape (e.g., a "C", "U", Figure 8 or hourglass shape) or a closed, non-overlapping shape (e.g., circle, oval, etc.).

Figure 5:
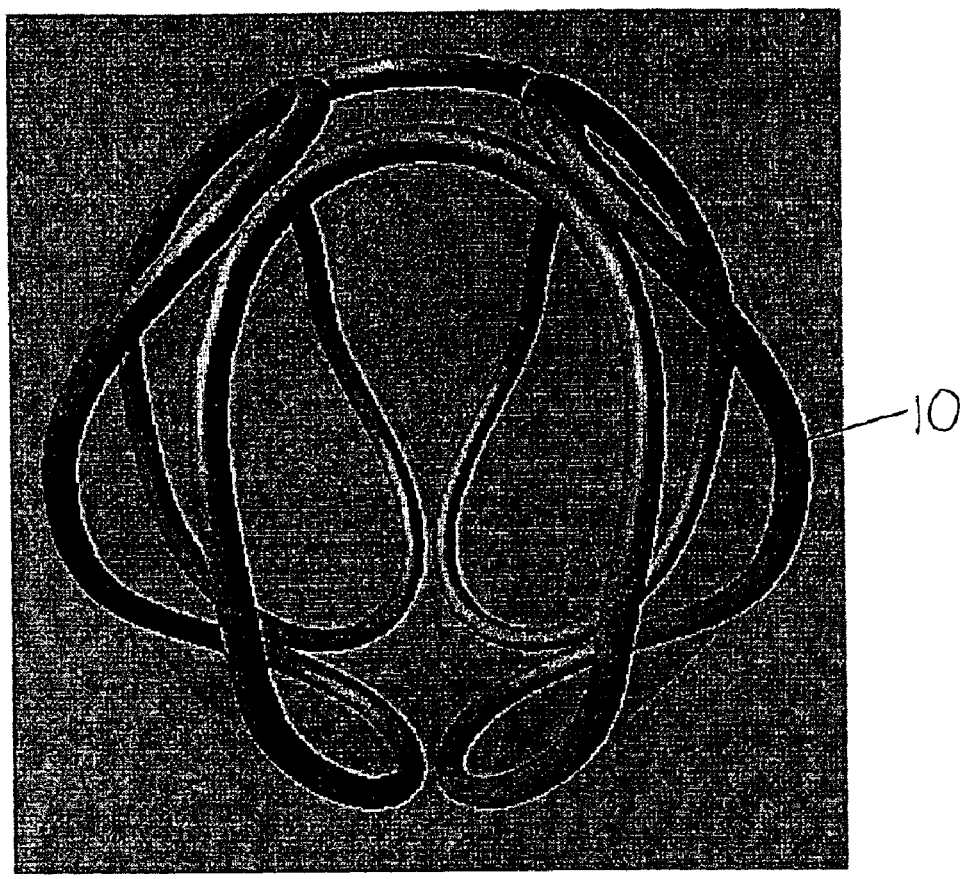
FIG. 5 depicts a non-overlapping device according to the present invention as deployed.
Figure 6:
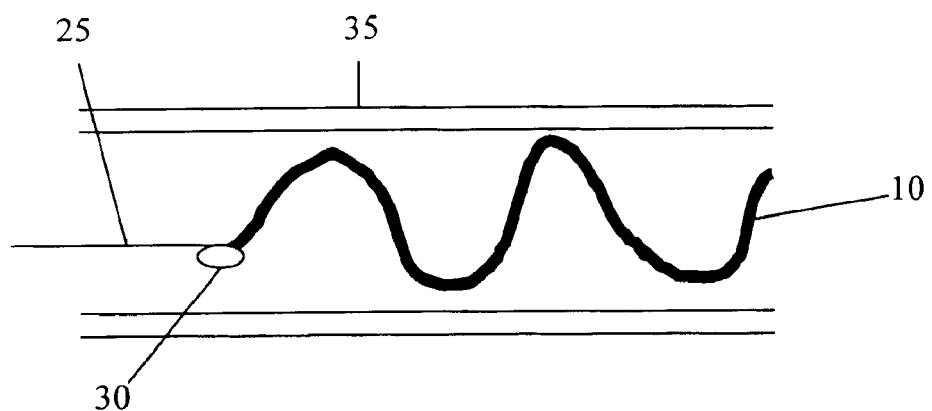
FIG. 6 depicts an exemplary non-overlapping device 10 as described herein in a linear primary configuration within a delivery catheter 35. Also depicted are detachment junction/deployment tip 25 at the proximal end of the device and pusher wire 30.

The non-overlapping devices described herein promote formation of a three-dimensional structure while minimizing rotation and whipping upon deployment. Thus, depending on the winding pattern and mandrel, the coil will readily self-form into its secondary, three-dimensional configuration and, accordingly, can be more easily deployed into a body cavity by the user. Determining the patterns, size and location to achieve the desired structures is within the purview of the skilled artisan in view of the teachings herein. The overall device is made up of a primary coil made from a wire. The primary coil is then wound into a secondary form, for example on a mandrel. The device is substantially straightened for deployment, for example, into a restraining member such as a deployment catheter. Upon release from the restraining member, the device self-forms into the secondary, relaxed, three-dimensional device. As shown, for example, in FIG. 5, a wire 10 is wound into a secondary configuration of non-overlapping turns. Further, as shown, the final shape of the secondary configuration (as deployed) can, in certain embodiments, approximate a sphere.

The material used in constructing the vaso-occlusive member (e.g., the wire) may be any of a wide variety of materials; preferably, the wire is a radio-opaque material such as a metal or a polymer. Suitable metals and alloys for the wire making up the primary coil include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biologically inert. Highly preferred is a platinum/tungsten alloy.

The wire may also be of any of a wide variety of stainless steels if some sacrifice of radiopacity may be tolerated. Very desirable materials of construction, from a mechanical point of view, are materials which maintain their shape despite being subjected to high stress. Certain "super-elastic alloys" include nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as a very small diameter wire. If a superelastic alloy such as nitinol is used in the device, the diameter of the coil wire may be significantly smaller than that used when the relatively more ductile platinum or platinum/tungsten alloy is used as the material of construction.

The coils may be made of radiolucent fibers or polymers (or metallic threads coated with radiolucent or radiopaque fibers) such as Dacron (polyester), polyglycolic acid, polylactic acid, fluoropolymers (polytetrafluoro-ethylene), Nylon (polyamide), or even silk. Should a polymer be used as the major component of the vaso-occlusive member, it is desirably filled with some amount of a known radiopaque material such as powdered tantalum, powdered tungsten, bismuth oxide, barium sulfate, and the like.

Generally speaking, when the device is formed of a metallic coil and that coil is a platinum alloy or a superelastic alloy such as nitinol, the diameter of the wire used in the production of the coil will be in the range of 0.0005 and 0.006 inches. The wire of such diameter is typically then wound into a primary coil having a primary diameter of between 0.005 and 0.035 inches. For most neurovascular indications, the preferable diameter is 0.010 to 0.018 inches.

We have generally found that the wire may be of sufficient diameter to provide a hoop strength to the resulting device sufficient to hold the device in place within the chosen body cavity without distending the wall of the cavity and without moving from the cavity as a result of the repetitive fluid pulsing found in the vascular system.

The axial length of the primary coil will usually fall in the range of 0.5 to 100 cm, more usually 2.0 to 40 cm. Depending upon usage, the coil may well have 100–400 turns per centimeter, preferably 200–300 turns per centimeter. All of the dimensions here are provided only as guidelines and are not critical to the invention. However, only dimensions suitable for use in occluding sites within the human body are included in the scope of this invention.

The overall diameter of the device as deployed is generally between 2 and 20 millimeters. Most aneurysms within the cranial vasculature can be treated by one or more devices having those diameters. Of course, such diameters are not a critical aspect of the invention.

Also contemplated in this invention is the attachment of various fibrous materials to the inventive coil for the purpose of adding thrombogenicity to the resulting assembly. The fibrous materials may be attached in a variety of ways. A series of looping fibers may be looped through or tied to coil and continue axially down the coil. Another variation is by tying the tuft to the coil. Tufts may be tied at multiple sites through the coil to provide a vast area of embolus forming sites. The primary coil may be covered by a fibrous braid. The method for producing the former variation is described in U.S. Pat. Nos. 5,226,911 and 5,304,194 to Chee. The method of producing the fibrous braid is described in U.S. Pat. No. 5,382,259, issued Jan. 17, 1995, to Phelps and Van.

The coils described herein can also include additional additives, for example, any material that exhibits biological activity in vivo. Non-limiting examples of suitable bioactive materials are known to those of skill in the art.

The inventive compositions may be associated with other materials, such as radioactive isotopes, bioactive coatings, polymers, fibers, etc., for example by winding, braiding or coating onto the device one or more of these materials, typically prior to introduction into the subject. Methods of associating polymeric materials with a solid substrate such as a coil are known to those of skill in the art, for example as described in U.S. Pat. Nos. 5,522,822 and 5,935,145. In yet other embodiments, the solid substrate itself is made to be radioactive for example using radioactive forms of the substrate material (e.g., metal or polymer). Polymeric or metallic substrates can be made radioactive by known methods such as electrodeposition (see, e.g., Hafeli et al. (1998) *Biomaterials* 19:925–933); ion beam deposition (see, e.g., Fehsenfeld et al. (1998) *Semin Interv Cardiol.* 3:157–161), impregnation techniques or the like. Thus, the solid substrates can be made to be radioactive after formation by deposition (e.g., coating, winding or braiding), impregnantion (e.g., ion-beam or electrodeposition) or other techniques of introducing or inducing radioactivity.

The mechanical occlusive devices may include a wide variety of synthetic and natural polymers, such as polyurethanes (including copolymers with soft segments containing esters, ethers and carbonates), ethers, acrylates (including cyanoacrylates), olefins (including polymers and copolymers of ethylene, propylene, butenes, butadiene, styrene, and thermoplastic olefin elastomers), polydimethyl siloxane-based polymers, polyethyleneterephthalate, crosslinked polymers, non-cross linked polymers, rayon, cellulose, cellulose derivatives such nitrocellulose, natural rubbers, polyesters such as lactides, glycolides, caprolactones and their copolymers and acid derivatives, hydroxybutyrate and polyhydroxyvalerate and their copolymers, polyether esters such as polydioxinone, anhydrides such as polymers and copolymers of sebacic acid, hexadecandioic acid and other diacids, orthoesters may be used. In a preferred embodiment, the polymeric filament comprises the materials of the present invention or other suture materials that have already been approved for use in wound heating in humans.

Methods of Making Non-Overlapping Three-Dimensional Coils

Vaso-occlusive devices are typically formed by winding a wire (e.g., a metallic wire) around a mandrel, for example winding the wire into a primary configuration such as a helical coil. The primary coil can be wound into a secondary form which can be straightened for deployment and self-form into a three-dimensional structure. Once wound onto a mandrel, the assembly of mandrel and coil is typically heat treated. The secondary form is one which, when ejected from a delivery catheter, forms a generally three-dimensional shape, conforming generally to the outer periphery of the target vessel. Desirably, the vaso-occlusive device is of a size and shape suitable for fitting snugly within a vascular cavity (e.g., an aneurysm, or perhaps, a fistula).

Suitable winding mandrels may be a variety of shapes (e.g., cylindrical, square, spherical, circular, rectangular, etc.) and may be solid or hollow. Some exemplary shapes of mandrels are shown in the FIGS. and in co-owned U.S. Pat. No. 5,957,948 to Mariant et al. As noted above, the winding mandrel is typically of sufficient heat resistance to allow a moderate annealing step. The mandrel may be made of a refractory material such as alumina or zirconia (for heat-treating devices made of purely metallic components) or may be made of a metallic material. Composite mandrels (e.g., composites of conductive and non-conductive materials) described in co-owned U.S. Ser. No. 09/637,470 may also be employed.

The winding mandrel should be of sufficient heat resistance to allow a moderate annealing step. A typical annealing step for a platinum/tungsten alloy coil would involve a 1100° F. heating step in air for about between about 15–20 minutes to about 6 hours. The mandrel may be made of a refractory material such as glass, alumina or zirconia (for heat-treating devices made of purely metallic components) or may be made of a metallic material (e.g., stainless steel). The pattern of winding on the mandrel provides both the three dimensional shape of the invention at deployment and also determines which areas of the coil are in contact with which areas of the mandrel.

Thus, the non-overlapping three-dimensional devices described herein are typically made by winding a wire onto a mandrel into a configuration that can be substantially straightened for deployment and self-forms into the three-dimensional configuration. FIG. 1 shows one exemplary pattern of winding to produce a non-overlapping three-dimensional device in which a wire 15 is wound into a Figure 8 shape in which the diameter of each loop is essentially equivalent. The mandrel is not shown in this Figure and the pattern of winding is depicted in two dimensions. Also shown in FIG. 1 are potential areas of which may be made "softer" 20 to help promote coil formation in situ. Methods of making selectively soft coils are described, for example, in co-pending U.S. Ser. No. 09/637,470.

Figure 2:
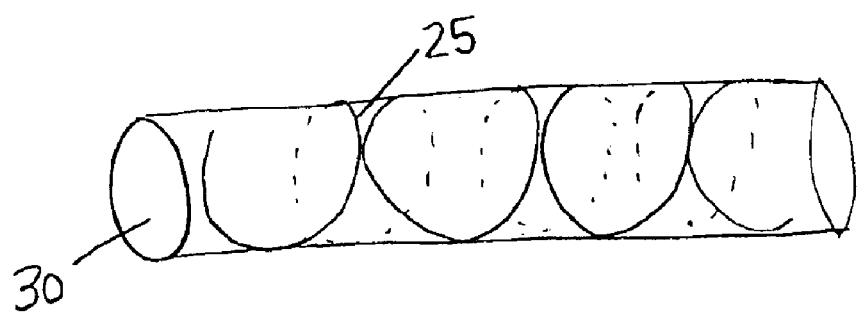
FIG. 2 depicts a wire wound around a cylindrical mandrel in a pattern that will create a non-overlapping three-dimensional vaso-occlusive device.
Figure 4:
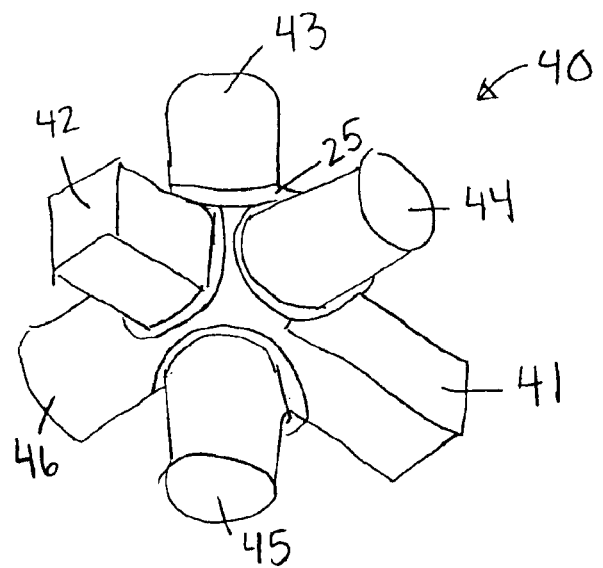
FIG. 4 depicts a wire wound around a six post mandrel to form a non-overlapping three-dimensional vaso-occlusive device.

FIG. 2 depicts how a wire 25 is wound around a cylindrical mandrel 30 to form the non-overlapping devices described herein. As shown in FIG. 1, the basic pattern used is a Figure 8. FIG. 4 shows a wire 25 wound about a 6-post mandrel 40 in a variation of the Figure 8 pattern.

Figure 3:
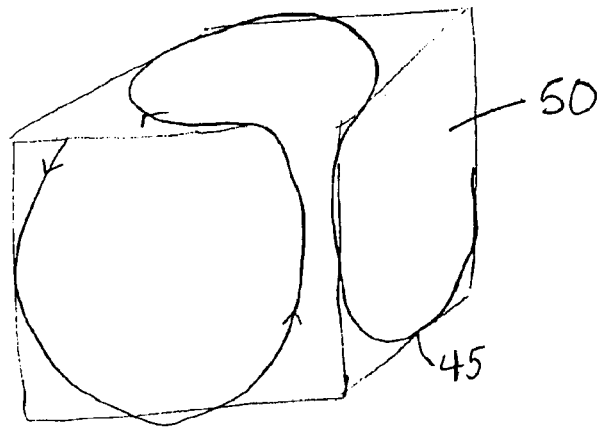
FIG. 3 depicts a wire wound around a three-dimensional mandrel. The mandrel may include channels to guide the wire as it is wound around the mandrel.

FIG. 3 shows yet another mandrel in which a primary coil 45 is wound around a three-dimensional mandrel 50. Circumferentially continuous grooves (not shown) on the surface of the mandrel may be preferably provided to assist in regularly aligning the strand as it is being wound about the core.

FIG. 4 shows a 6-post mandrel 40 suitable for forming a device described herein. As will be apparent from the teachings herein, the winding mandrel can include any number of posts and each post can be of virtually any shape. Shown in FIG. 4 is a 6 post winding mandrel 40 with two square posts 41, 42 and four round posts 43, 44, 45, 46. Further, in certain embodiments, each post is positioned at approximately 90° relative to the other posts.

The winding mandrel is typically made of a refractory material, such as alumina or zirconia, primarily to form a support for winding that will not pollute the vaso-occlusive device during the heat-treatment step to be described below, and will provide a the three-dimensional form for the vaso-occlusive device during the heat-treatment step. Additionally, a small strand receptacle may be provided to insert and hold the end or ends of the strand in place when performing the heating step.

Other methods of winding a strand around a core will be apparent to one skilled in the art. The continuous grooves are preferably provided to permit the strand to be wound about the core such that the resulting three-dimensional configuration contains non-overlapping loops, for example, by providing Figure 8 shaped channels in a spherical mandrel. The continuous grooves, reduce or eliminate the 90° plane positions associated with whipping upon deployment of vaso-occlusive coils. Alternatives to grooved mandrels, include, for example, using mandrels with pins or other protruding structures to provide guides for winding the primary configuration. Spherical mandrels with continuous grooves therein can be encapsulated in half-bricks with hollow half spheres cut out for annealing.

Methods of Use

The non-overlapping, three-dimensional devices described above are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the mechanical devices prior to introducing the inventive composition. Shortly after the mechanical devices and the inventive composition are placed within the aneurysm, an emboli begins to form and, at some later time, is at least partially replaced by neovascularized collagenous material formed around the vaso-occlusive devices.

In using the occlusive devices of the present invention, a selected site is reached through the vascular system using a collection of specifically chosen catheters and guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter as a unit. Once the tip of the guidewire reaches the end of the guiding catheter, it is then extended using fluoroscopy, by the physician to the site to be treated using the vaso-occlusive devices of this invention. During the trip between the treatment site and the guide catheter tip, the guidewire is advanced for a distance and the neurovascular catheter follows. Once both the distal tip of the neurovascular catheter and the guidewire have reached the treatment site, and the distal tip of that catheter is appropriately situated, e.g., within the mouth of an aneurysm to be treated, the guidewire is then withdrawn. The neurovascular catheter then has an open lumen to the outside of the body. The devices of this invention are then pushed through the lumen to the treatment site. They are held in place variously because of their shape, size, or volume. These concepts are described in the Ritchart et al patent as well as others. Once the vaso-occlusive devices are situated in the vascular site, the embolism forms.

The mechanical or solid vaso-occlusion device may be used as a kit with the inventive polymeric composition.

Modifications of the procedure and device described above, and the methods of using them in keeping with this invention will be apparent to those having skill in this mechanical and surgical art. These variations are intended to be within the scope of the claims that follow.

What is claimed is:

1. A vaso-occlusive device comprising at least one substantially linear strand of a vaso-occlusive member wound into a stable, three-dimensional relaxed configuration comprising a plurality of non-overlapping loops, wherein said relaxed configuration self-forms upon release from a restraining member.

2. The vaso-occlusive device of claim 1, wherein the relaxed configuration fills a body cavity.

3. The vaso-occlusive device of claim 1, wherein the relaxed configuration approximates a sphere.

4. The vaso-occlusive device of claim 1, comprising between 6 and 20 loops.

5. The vaso-occlusive device of claim 1, comprising between 6 and 12 loops.

6. The vaso-occlusive device of claim 1, wherein the vaso-occlusive member comprises a metal selected from the group consisting of platinum, palladium, rhodium, gold, tungsten and alloys thereof.

7. The vaso-occlusive device of claim 1, wherein the vaso-occlusive member comprises a stainless steel or super-elastic metal alloy.

8. The vaso-occlusive device of claim 1, wherein the vaso-occlusive member comprises nitinol.

9. The vaso-occlusive device of claim 1, further comprising additional filamentary material attached to the vaso-occlusive member.

10. The vaso-occlusive device of claim 1, further comprising a deployment tip attached to at least one of the two ends of the vaso-occlusive member.

11. The vaso-occlusive device of claim 10, wherein the deployment tip comprises a mechanically detachable end adapted to attach and detach from a pusher.

12. The vaso-occlusive device of claim 10, wherein the deployment tip comprises an electrolytically detachable end adapted to detach from a pusher by imposition of a current on the pusher.

13. A method of occluding a body cavity comprising introducing a vaso-occlusive device according to claim 1 into the body cavity.

14. The method of claim 13, wherein the body cavity is an aneurysm.

15. A method of making a non-overlapping three-dimensional vaso-occlusive device according to claim 1, the method comprising
    (a) winding a substantially linear strand of a vaso-occlusive member around a winding mandrel, said winding comprising a winding pattern that produces a non-overlapping three-dimensional vaso-occlusive device according to claim 1; and
    (b) heating the mandrel and vaso-occlusive member to produce said vaso-occlusive device.

16. The method of claim 15, wherein the winding pattern is a Figure 8 or hourglass.

17. The method of claim 15, wherein the winding mandrel comprises a sphere having grooves adapted to fit the substantially linear strand.

18. The method of claim 15, wherein the winding mandrel comprises a cylinder.

19. The method of claim 15, wherein the winding mandrel comprises a sphere having a plurality of pins on the surface thereof.

20. The method of claim 15, wherein the winding mandrel comprises a tetrahedron.

21. The method of claim 15, wherein the winding mandrel comprises 3 intersecting posts which form a 6 post structure and wherein each post is at approximately 90 relative to the adjacent posts.

22. The method of claim 21, wherein at least one post has a round cross section.

23. The method of claim 21, wherein each post has a round cross section.

* * * * *